United States Patent [19]

Grynberg et al.

[11] Patent Number: 4,492,862
[45] Date of Patent: Jan. 8, 1985

[54] METHOD AND APPARATUS FOR ANALYZING COMPONENTS OF HYDROCARBON GASES RECOVERED FROM OIL, NATURAL GAS AND COAL DRILLING OPERATIONS

[75] Inventors: Jack Grynberg, Englewood, Colo.; Leonard Y. Nelson, Seattle; Stephen E. Moody, Kirkland, both of Wash.

[73] Assignee: Mathematical Sciences Northwest, Inc., Bellevue, Wash.

[21] Appl. No.: 290,824

[22] Filed: Aug. 7, 1981

[51] Int. Cl.³ ............................................... G01V 5/00
[52] U.S. Cl. ...................................... 250/255; 250/343
[58] Field of Search ............... 250/254, 255, 339, 340, 250/341, 343, 345

[56] References Cited

U.S. PATENT DOCUMENTS 2,280,075  4/1942  Hayward .
2,573,390  10/1951  Blanchard .
2,745,282  5/1956  Rochon .
2,761,975  9/1956  Weisz ............................... 250/255 X
2,786,144  3/1957  Weisz .................................. 250/255

(List continued on next page.)

OTHER PUBLICATIONS

Exhibit 1—C. Forbes Dewey, Jr., "The MIT Two-Wavelength Laser System for Measuring Atmospheric Methane". Text of talk presented at a meeting on Current Research on Methane Detection & Measurement, sponsored by Gas Research Institute, Chicago, Ill., Aug. 27, 1979.

Exhibit 2—Dewey et al., "Acoustic Amplifier for Detection of Atmospheric Pollutants", *Applied Physics Letters*, vol. 23, No. 11, Dec. 11, 1973.

Exhibit 3—H. J. Gerritsen, "Tuned-Laser Spectroscopy of Organic Vapors", in *Physics of Quantum Electronics*, Kelly, Lax & Tannelwald, Eds. (McGraw-Hill, NY 1966, p. 581 et seq.).

Exhibit 4—Balakin et al., "Switching of the Emission Wavelength of a Helium-Neon Laser in the 3.39μ region", *Sov. J. Quant. Electron.*, vol. 5, No. 2, Aug. 1975, pp. 230, 231.

Exhibit 5—H. J. Gerritsen, "Methane Gas Detection Using a Laser", *Transactions*, Dec. 1966, pp. 428, 429, 430, 431, 432.

(List continued on next page.)

*Primary Examiner*—Janice A. Howell
*Attorney, Agent, or Firm*—Christensen O'Connor Johnson & Kindness

[57] ABSTRACT

Beams (11) and (13) produced by helium-neon gas lasers (10) and (12) are directed at photoacoustic absorption cells (20) and (21) containing a flowing sample gas stream recovered from coal, oil and natural gas well drilling. The common hydrocarbon gases and vapors within cell (20) highly absorb the infrared energy emitted by laser (10) thereby producing an acoustic disturbance which is detected by a transducer (34) which produces an electrical output signal proportional to the concentration of the hydrocarbon gases and vapors. The methane gas within cell (21) weakly absorbs the infrared energy of laser beam (13), and thus the resulting output signal produced by a transducer (35) serves as a reference signal for determining the methane concentration. The output signals from transducers (34) and (35) are used by data processing unit (40) to compute the total concentration of hydrocarbon gases and vapors and the concentration of methane gas within cells (20) and (21). A turnable carbon dioxide gas laser (44) produces laser beams (45) and (47) both in the infrared region which are highly absorbed by the propane and n-butane component gases, respectively, flowing through photoacoustic cell (48). The level of energy absorbed from these two beams, as determined by the energy of the acoustic disturbance produced within cell (48) induces production of an electrical output signal by transducer (56) at levels proportional to the concentrations of the propane and n-butane gases in cell (48). The output signals from transducer (56) are then used by data processing unit (40) to compute the concentrations of propane, n-butane gases and $C_5^+$ gases in the sample.

88 Claims, 1 Drawing Figure

Fig. 1.

METHOD AND APPARATUS FOR ANALYZING COMPONENTS OF HYDROCARBON GASES RECOVERED FROM OIL, NATURAL GAS AND COAL DRILLING OPERATIONS

DESCRIPTION

FIELD OF THE INVENTION

The present invention relates to natural gas and oil well mud logging and coal bore hole logging, and more particularly to methods and apparatus for analyzing the composition of the hydrocarbon gases and vapors entrapped in the drilling mud by measuring the absorption of various laser beams by the hydrocarbon gases and vapors.

BACKGROUND ART

In the exploration and development of oil and natural gas and coal deposits, during well drilling operations, drilling mud is circulated down through a hollow drilling string (drill stem) of a down hole pipe to both cool and lubricate the drill bit, as well as bring to the surface the formation cuttings from the hole. The mud is recovered by passing it up around the outside of the drill bit and the rotating drill stem which powers the bit. During its circulation through the drill hole, the mud entraps various types of gases and vapors, including any hydrocarbons which are present in the strata drilled through. As the mud is recovered from the hole, the entrapped gases are liberated from the mud and measurements are made to sense the presence of hydrocarbon gases and vapors and to determine the chemical composition of the gases and vapors. This information is useful in determining whether or not oil, natural gas or coal accumulations are located in strata penetrated by the drilling bit.

Hydrocarbon gases and vapors which are entrapped in drilling mud may be composed of a mixture of various types of alkanes ($C_nH_{2n+2}$) including methane, ethane, propane, n-butane, iso-butane, pentane, hexane, heptane, etc., which are typically present in continuous underground commercial reservoirs of oil, natural gas or coal. An accurate estimation of the presence of oil or natural gas requires not only the detection of the presence of hydrocarbon gases and vapors, but also the proportions of the types of constituent gases composing the hydrocarbon gas mixture.

The detected presence of methane gas indicates merely that some type of decayed organic material is present such as in a discontinuous reservoir usually referred to as a "pocket". However, such information may be useful in searching for coal seams, where the detection of methane during bore hole drilling at appropriate depths may mean the discovery of a useful deposit of coal. Although the presence of methane may also provide an initial indication of an oil or natural gas find, the presence of heavier molecular weight hydrocarbons provides an important confirmation of such a find, and may prevent a misleading conclusion associated with non-commercial presence of pockets of swamp gas. The heavier $C_2$–$C_{10}$ hydrocarbons are not commonly found in living organisms and recent geological sediments but form a significant part of many commercial natural gas and crude oil deposits. The source of the carbonaceous material which generates these higher alkanes is an intermediate, polymeric material known as kerogen, which is a conglomeration of various chain hydrocarbons. The detection of heavier molecular weight hydrocarbon gases and vapors, such as butane and propane, signifies that an oil or natural gas reservoir may have been penetrated by the drill bit.

In the past, analysis of the composition of the hydrocarbon gas mixture entrapped in drilling mud has been carried out principally by use of a gas chromatograph. A gas chromatograph consists basically of a column filled with various types of packing material to separate the components of the hydrocarbon gas recovered from the drilling mud. As a sample of the hydrocarbon gas is passed through the tube, the different components of the gas exit the tube at different times depending on the boiling point of the components and their affinity to the different types of packing material. The discharge of the constituent gases from the column may be detected by changes in the electrical conductivity of a filament disposed at the discharge end of the column. The conductivity of the filament is dependent on the composition of the gas passing over the filament. Alternatively, a hydrogen flame may be located at the discharge end of the column, which flame creates ions which are sensed by appropriate instrumentation.

Gas chromatographs have operating characteristics which limit their usefulness in mud logging. The chromatographs do not operate properly when very large concentrations of hydrocarbon gases are present within the mud system. Also, due to the time span needed to analyze gases, the gases are sampled only on an intermittent batch basis. During the time interval between two sample batches, the drill bit may have already passed through a potentially productive reservoir horizon known as the "pay zone" where a commercial hydrocarbon accumulation may be entrapped. Thus, the gas chromatograph may miss the "pay zone" entirely. In addition, many types of gases recovered from oil and natural gas wells, such as hydrogen sulfide are corrosive thereby not only limiting the useful life of a chromatograph electrical filament, but also making it difficult to calibrate the detector. The hydrogen flame type detector requires the use of hydrogen gas which frequently is not conveniently available at remote drilling sites.

It is a principal object of the present invention to provide a method and apparatus for accurately, quickly and safely detecting, identifying and measuring the constituent hydrocarbon gases removed from drilling mud. It is known that certain frequencies of electromagnetic radiation in the infrared spectral region are highly absorbed by gases while other frequencies of infrared radiation are not absorbed or are only weakly absorbed. The highly absorbed frequencies correspond to the natural vibrational frequencies of the atoms of the gas molecules. In the present invention, lasers, which emit narrow line-width infrared radiation at frequencies corresponding to the absorption frequencies of hydrocarbon gases and vapors, are used to detect specific components in the gas samples removed from the drilling mud. The energy absorbed by the gas sample is measured at particular laser frequencies by photoacoustic absorption techniques to identify and quantify the individual gas components thereof.

In the past, lasers have been proposed for geologic exploration. U.S. Pat. No. 4,247,770 discusses the use of a laser carried by an aircraft to conduct aerial mineral surveys. The laser directs a pulsed beam at a point on the earth's surface to vaporize the material at the point of contact and generate an atomic emission spectra characteristic of the vaporized material. A spectrometer carried in the aircraft collects and analyzes the resultant spectra to determine the type and quantity of chemical elements present in the vaporized sample. A second, lower power laser may be then used to illuminate the vaporized material produced by the first, high power laser to generate the Raman spectrum of the vaporized material before it diffuses. After the vaporized material has diffused, the second laser may be used to illuminate the earth surface which has been freshly cleared by the high power laser beam to yield a fluorescent spectrum which also can be analyzed for mineral content.

Helium-neon laser systems have been used to measure methane. In an article by Grant et al. titled "Laser System for Global Detection of Natural Gas", published by Jet Propulsion Laboratory, Pasadena, CA., Second Quarterly Report, Apr. 20, 1981, GRI Contract No. 5080-352-0327, NASA Contact NAS7-100, the feasibility of utilizing lasers for the remote detection of leaks associated with storage, transportation and delivery of natural gases was explored. A system is proposed which utilizes a pair of helium-neon lasers to emit a first laser beam at a frequency strongly absorbed by methane gas and a second laser beam at a frequency weakly absorbed by methane gas. The extent to which the two laser beam frequencies are absorbed is measured by an InSb detector. A drawback of this particular system is that for accurate measurements, the detector must be maintained at a low temperature of approximately 77° Kelvin. The cooling system needed to maintain the detector at such a low temperature is not only complicated, but also expensive to construct and maintain. Furthermore, this approach only yields quantitative data relating to the methane content of the gas sample. Specific information regarding the heavier hydrocarbon composition of the mixture is not obtainable from the two frequency helium-neon laser approach.

Gerritsen in an article titled "Methane Gas Detection Using a Laser", published in *American Institute of Mining Engineers,* Vol. 235 at 428 (1966), also discusses the use of a dual frequency helium-neon laser system to sense the presence of methane gas. A lead sulfide photoconductor is used to measure the extent to which the methane gas absorbs the energy of the laser beams.

R. M. Russ, Jr. in his masters thesis submitted at the Massachusetts Institute of Technology in June, 1978, describes another helium-neon system for measuring methane in the vicinity of a liquified natural gas spill. The system involves an etalon technique for deriving two separate analysis frequencies from a single helium-neon laser.

All of the laser systems discussed above, except the one described in the '770 patent, are intended only for methane detection. They cannot provide quantitative information regarding other hydrocarbon gases and vapors such as propane and butane. The laser system used in the '770 patent excites atomic emission, atomic Raman and fluorescences spectra and thus does not involve the infrared spectra employed in the present invention.

DISCLOSURE OF THE INVENTION

The present invention relates to a method and apparatus for detecting and measuring the composition of all of the principal hydrocarbon gases and vapors entrapped in oil and natural gas well drilling mud or found in coal bore hole effluent to facilitate the precise location of promising oil and natural gas reservoirs and coal horizons. A first helium-neon gas laser beam, having an infrared radiation frequency strongly absorbed by all the hydrocarbon gases and vapors, including methane gas, is directed at a first photoacoustic absorption cell through which a continuous flow of the gas recovered from the drilling mud or coal bore hole effluent is passed. The absorption cell contains a microphone which serves as a highly sensitive pressure transducer. Gases or vapors which absorb the incident laser radiation convert this energy to thermal motion and hence create an acoustic pressure disturbance, such as a wave, which is sensed by the transducer. The transducer produces an output electrical signal which is proportional to the energy absorbed by the hydrocarbon gas molecules. The energy absorbed from the first laser beam in turn is proportional to the concentration of all the hydrocarbon gases (denoted by "$C_1-C_6^+$") in the flowing sample.

A second helium-neon gas laser beam having an infrared radiation frequency absorbed by most types of hydrocarbon gases except methane (denoted by $C_2-C_6^+$) is directed at the flowing gas sample housed in a second photoacoustic cell. In this instance, the energy absorbed from the second laser beam is detected by a transducer mounted on the second photoacoustic cell which produces an electrical output signal representative of the proportion of the $C_2-C_6^+$ hydrocarbon gases and vapors present in the gas sample.

Thus, the difference in the levels of the first and second output signals of the transducers is indicative of the quantity of methane gas present in the gas sample. The output signals of the transducers are first amplified and then utilized by a data processing unit to calculate the $C_1-C_6^+$, $C_2-C_6^+$, and methane gas concentrations.

The present invention also includes directing third and fourth laser beams generated by a carbon dioxide gas laser at a third photoacoustic cell which also contains a flowing sample of the gas recovered from the drilling mud. The third beam is selective for measuring a particular type of hydrocarbon gas such as propane, while the fourth beam is specific to another type of hydrocarbon gas such as butane. A diffraction grating is utilized to tune the carbon dioxide (hereafter "$CO_2$") laser to various infrared output frequencies which are selectively absorbed by the hydrocarbon gases such as propane and n-butane. At a few particular frequencies the other constituent gases which comprise the hydrocarbon gas mixture will absorb very little of the energy of the $CO_2$ laser beam while substantially all of the energy absorbed is due to the presence of propane or n-butane gas. Consequently, quantitative measurement of the presence of propane or n-butane gas does not require the use of a second, reference laser beam which is emitted at a frequency which is weakly absorbed by propane or n-butane gases.

The absorption of the energy of the third laser beam is also measured using photoacoustic methods. The acoustic signal generated by the absorption of the third laser beam is proportional to the propane concentration in the flowing gas sample. The transducer produces an output electrical signal proportional to the extent to which the third laser beam energy is absorbed by the propane gas. The output signal of the transducer is amplified and then processed by a data processing unit to calculate the propane gas concentration.

The diffraction grating may be switched from its orientation at which the laser emits the third laser beam frequency to a second position at which the laser produces a fourth beam at an infrared frequency which is strongly absorbed by n-butane gas and in proportion to the concentration of n-butane gas present, and not significantly absorbed by any other types of hydrocarbon gases. As an alternative, two separate $CO_2$ lasers can be used to generate the necessary frequencies, thereby eliminating the need to switch the grating position. The quantity of n-butane in the sample gas is determined by measuring the extent to which the energy of the fourth laser beam is absorbed by the gas. As in the above-described constituent gas detection methods, this is accomplished by use of the third transducer which produces an output electrical signal which is proportional to the acoustic disturbance generated by the n-butane absorption of the fourth laser beam. The acoustic disturbance generated by the fourth laser beam is proportional to energy of the fourth laser beam absorbed by the gas and which in turn is proportional to the concentration of n-butane gas present. The fourth output signal is also amplified and then processed by the processing unit to compute the quantity of n-butane gas present in the gas sample.

The above-described methods of measuring the concentration of propane and n-butane gas in the gas sample assume that the presence of any other types of hydrocarbon gases does not significantly attenuate the energy of the carbon dioxide laser beam. However, it is known that some attenuation is in fact caused by other hydrocarbon gases. Accordingly, the accuracy of the above-described method of measuring the concentrations of propane and n-butane gases may be enhanced by adjusting the propane and n-butane measurements by a factor corresponding to the ratio of the lighter to heavier molecular weight hydrocarbon gases comprising the gas sample. This adjusting factor is calculated by use of the above-described output signals produced by the helium-neon laser beams. As noted above, the first output signal corresponds to the concentrations of total hydrocarbon gases present while the second output signal is indicative of the hydrocarbon gases minus the methane gas present.

The present invention addresses a particular problem associated with coal bore hole drilling. In coal exploration and development drilling operations, often times air rather than mud is pumped down through a hollow drilling string to cool and lubricate the bit and to carry the coal cuttings to the surface. However, because of the friability of coal, coal chips continue to rise to the surface long after the drill bit has passed the interval of the coal horizon. Consequently it is difficult to determine the true depth of the coal horizon from monitoring the presence of coal cuttings in the well drilling effluent. Hence a rapid hydrocarbon gas analysis system is important to establishing the depth and thickness of the coal horizon. The present invention provides a fast and accurate means for monitoring the hydrocarbon gases, primarily methane, which emanate from a coal deposit and therefore provides a measure of the depth and thickness of the coal deposit drilled through by the bit.

In addition to oil and natural gas well and coal bore hole drilling operations, the present invention may be used in conjunction with coring operations, such as during the exploration and development of oil shale deposits. Hydrocarbon bases recovered during coring operations can be analyzed to determine their identity and concentrations. Accordingly, it is to be understood that in the present application the term "drilling" is also meant to encompass coring operations.

BRIEF DESCRIPTION OF THE DRAWINGS

The details of one typical embodiment of the present invention will be described in connection with the accompanying drawing labeled FIG. 1, which is a schematic view of a system for analyzing the components of hydrocarbon gases recovered from oil and natural gas well and coal bore hole drilling through the use of lasers which emit beams at frequencies corresponding to the natural vibration frequencies of various component hydrocarbon gases.

BEST MODE OF THE INVENTION

Figure 1:
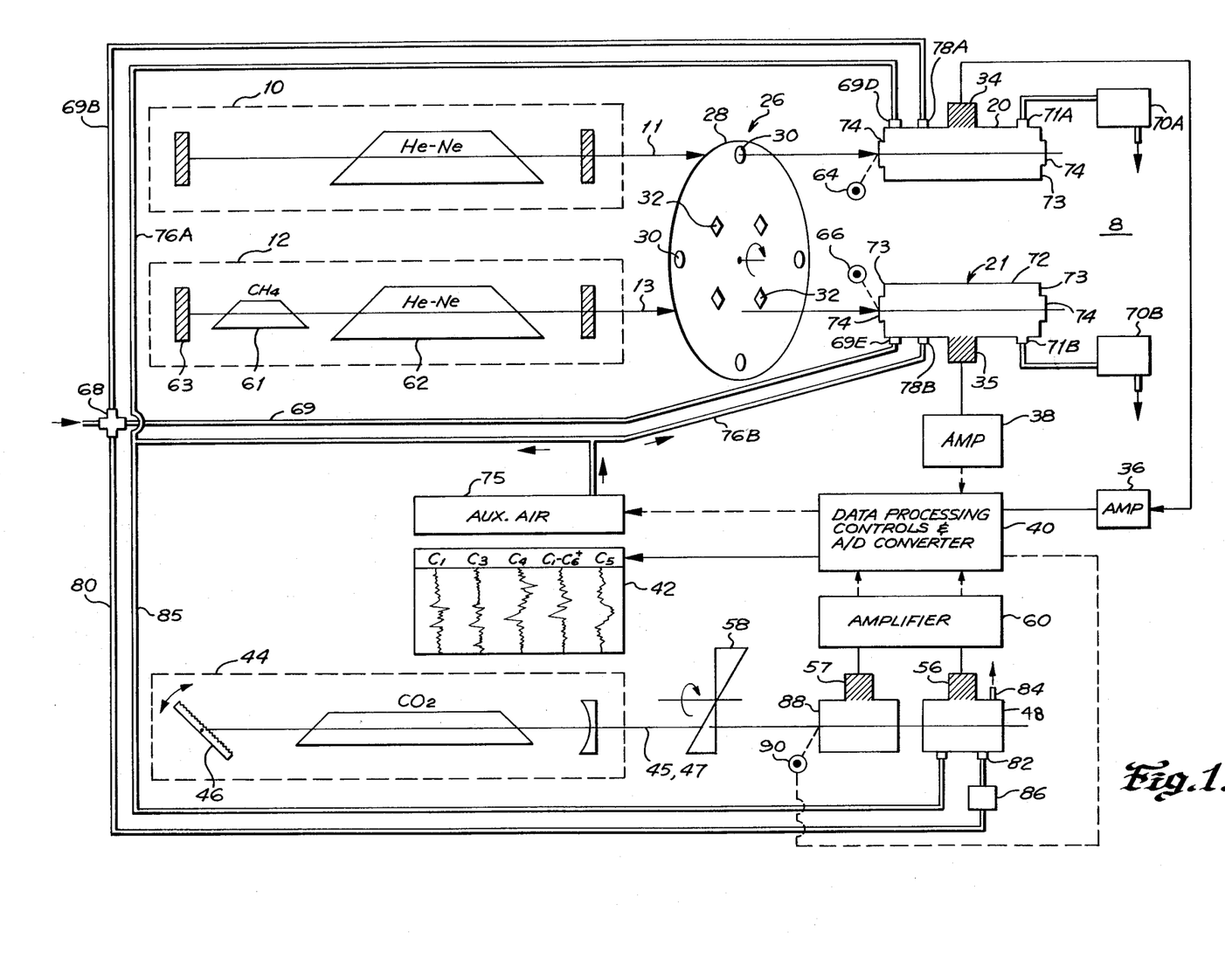

Referring initially to the drawing, a system 8 constructed according to the best mode of the present invention currently known to the applicants for determining the composition of gases and vapors recovered from oil and natural gas well drilling mud or coal bore hole drilling effluent is schematically illustrated. In basic form, system 8 includes a first helium-neon gas laser 10, producing an output beam 11 having a natural wavelength in the infrared region which is strongly absorbed by most types of hydrocarbon vapors and gases including methane. A second helium-neon laser 12 is tuned to produce a second output beam 13 in the infrared frequency range which is absorbed by most hydrocarbon vapors and gases except methane gas. Beam 11, produced by laser 10, is directed to pass through a first photoacoustic absorption cell 20. Cell 20 contains gases which are recovered from drilling mud used to lubricate the drill bit at the bottom of a drill string in an oil or natural gas drilling operation, or derived from coal bore hole drilling operations. The recovered gas may include various compositions of hydrocarbon gases typically present in continuous, underground reservoirs of natural gas, oil or coal. The method and apparatus used to recover the gases from the drilling mud or bore hole effluent are well-known in the art and do not form a portion of the present invention. Preferably the recovered gases are continuously circulated through photoacoustic cell 20 so that the composition of the recovered gases may be continuously analyzed in real time.

The second helium-neon laser 12 is aligned so that its output beam 13 enters a second photoacoustic cell 21 which contains the same sample gases as in cell 20. Beams 11 and 13 are transformed into pulsed beams through the use of a switching device in the form of chopper 26 having a perforated wheel 28 rotating at approximately 1K Hz which speed is sufficiently fast to minimize mechanical noise occurring at lower frequencies. Wheel 28 has a first set of openings 30 disposed about its axis or rotation which align with beam 11 to allow the beam to pass through the wheel and strike photoacoustic absorption cell 20. Wheel 28 also includes a second set of openings 32 aligned with the beam 13 to allow the beam to strike cell 21. The hole patterns are configured such that for a certain interval of time the beams are blocked.

The energy absorbed by the methane and other hydrocarbon gases present in the sample mixture flowing through cell 20 produces an acoustical disturbance, such as a wave, which is sensed by a very sensitive pressure transducer 34. Transducer 34 produces an output electrical signal proportional to the acoustical disturbance generated by the gas sample housed within cell 20 which in turn is proportional to the level of infrared energy absorbed from beam 11. The latter level can be used to derive the total hydrocarbon gas concentration in cell 20. The output electrical signal produced by transducer 34 is amplified by amplifier 36 and then converted to a digital signal by a data processing unit 40. Data processing unit 40, which is synchronized to the orientation of chopper wheel openings 30 continuously calculates the signal levels during the opening of the chopper for beam 11 and then subtracts any background noise measured when the laser is blocked.

Similarly, the energy absorbed by the hydrocarbon gas content minus the methane present in the sample flowing through cell 21 produces an acoustical disturbance which is sensed by a second transducer 35. Transducer 35 produces an output electrical signal proportional to the acoustic disturbance generated by the gas sample within cell 21 which in turn is proportional to the level of infrared energy absorbed from beam 13 and which in turn can be used to derive the hydrocarbon gas minus the methane concentration in cell 21. The output electrical signal produced by transducer 35 is amplified by second amplifier 38 which is then converted into a digital signal by data processing unit 40. The data processing unit is synchronized to the orientation of chopper wheel openings 32. It then continuously calculates the signal levels during the opening of the chopper for beam 13 and subtracts any background noise measured when the laser beam is blocked.

Data processing unit 40 processes the absorption signals from transducers 34 and 35 to determine the concentration of total hydrocarbon gases and vapors present in the gas sample contained in cells 20 and 21 and also the concentration of methane gas contained within the sample. These two different concentrations are shown on display 42 for evaluation and use by geologists or petroleum engineers.

The present invention also includes a $CO_2$ gas laser 44 which is frequency tuned by a diffraction grating 46 which is adjustable between a first position tuning the laser to produce a third beam 45 in the infrared region which is strongly absorbed by propane gas, as well as by the small quantities of hexane present, and somewhat less by the small quantities of pentane and heptane present; and a second position tuning the laser to produce a fourth beam 47 in the infrared region which is strongly absorbed by n-butane gas but only weakly by other types of hydrocarbon gases. Laser 44 is aligned so that the third and fourth output beams 45 and 47 pass through a third photoacoustic cell 48 which also contains gases to be analyzed.

The infrared energies absorbed from third and fourth laser beams 45 and 47 excite the propane and n-butane components respectively, of the hydrocarbon gas contained in cell 48. The acoustic disturbance generated by the excited propane and n-butane molecules are detected by a very sensitive third transducer 56 mounted on cell 48. Transducer 56 produces an output electrical signal proportional to the acoustic disturbance generated by the propane and n-butane gases which in turn is proportional to the level of the infrared energy absorbed by these gases and which in turn is proportional to the concentration of propane and n-butane gas in the cell. The beams produced by the continuous-wave $CO_2$ laser 44 are converted into a pulsed source by a switching mechanism in the form of mechanical chopper 58 disposed between laser 44 and cell 48. Two alternative chopping methods may be used. The first being to replace the continuous-wave laser with a pulsed type laser, while the second is to employ a crystal type beam modulator (not shown) in place of the mechanical chopper wheel 58. The alternating signals are amplified by amplifier 60. The output from amplifier 60 is transformed by data processing unit 40 into the actual concentration of propane, n-butane and aggregate pentane plus heavier molecular weight hydrocarbon (hereafter "$C_5+$") gases present in photoacoustic cell 48.

Data processing unit 40 utilizes the output signals received from amplifiers 36 and 38 to adjust the measured concentrations of propane, n-butane and $C_5+$ gases to produce a more accurate reading thereof. The proportion of methane gas contained within cells 20, 21 and 48 can be determined from the output signals of amplifiers 36 and 38 which also provide an indication of the concentration of the heavier molecular weight hydrocarbon gases contained within these three cells. This information may be used to adjust the propane, n-butane and $C_5+$ concentrations as determined from the signals received from amplifier 60, which adjusted values are shown on display 42 for use by geologists or petroleum engineers. Moreover this information can also be used to estimate the pentane and hexane composition in the gas sample.

Considering the above, briefly described, method and apparatus of the present invention in more detail, lasers 10 and 12, utilizing a mixture of helium and neon gas as a working medium, emit beams 11 and 13, respectively, in the infrared region which is in the molecular absorption spectrum of most hydrocarbon gases. Beam 11, emitted from laser 10 at a frequency of approximately 2,947.91 cm$^{-1}$, is strongly absorbed by methane and the other types of hydrocarbon gases within cell 20. Thus, the energy absorbed from beam 11 is indicative of the total $C_1$-$C_6+$ gas content within photoacoustic cell 20. This information provides the geologist and petroleum engineer with an initial indication that natural gas, or oil or coal horizons, have been or are being penetrated.

However, since the detected hydrocarbon gas may be from other sources, it is desirable to analyze the composition of the hydrocarbon gas for components known to be present in natural gas and/or oil, as well as coal. This is, in part, accomplished by utilizing laser 12 in conjunction with laser 10 to measure the level of methane gas. This information is helpful since natural gas is composed primarily of methane gas and methane gas is associated with commercial oil and natural gas producing reservoirs. Laser 12 is designed to emit beam 13 at a frequency of approximately 2,948.78 cm$^{-1}$ which is weakly absorbed by methane gas. Thus, the difference in the levels of energies absorbed by the hydrocarbon gas mixture from beams 11 and 13 is indicative of the concentration of methane gas contained in photoacoustic cells 20 and 21.

This method of determining the methane gas concentration is especially accurate for "wet" hydrocarbon mixtures, i.e. those composed principally of heavier molecular weight gases such as propane, butane and pentane. However, in hydrocarbon gas mixtures consisting of higher proportions of lighter molecular weight gases ("dry" gas), such as methane and ethane, a larger proportion of the infrared energy from beam 13 is absorbed by methane, thus reducing the accuracy of the methane gas concentration measurement made by this method. This inaccuracy is the result of the residual methane absorption at the laser frequency of beam 13, which is accentuated at high methane concentrations. The methane absorption coefficient at this frequency can be reduced by operating the absorption cell at reduced total pressure thus considerably improving the accuracy of the methane concentration determination for the "dry" gas situation.

The ratio of energy absorbed from the first laser beam 11 to the energy absorbed from the second laser beam 13 provides an indication of average molecular weight of the hydrocarbon sample within cell 20. As discussed more fully below, applicant has used this ratio to refine the measured concentrations of propane, n-butane and $C_5^+$ gases determined through the use of $CO_2$ laser 44.

First laser beam 11 is emitted at a power output of approximately 1 milliwatt and at a frequency of approximately 2,947.9 cm$^{-1}$. This is the natural frequency of a helium-neon laser equipped with infrared reflective mirrors. The construction of lasers 10 and 12 are essentially the same with the exception that in laser 12 a gas cell 61 containing methane is inserted into the cavity between gas discharge tube 62 and reflecting mirror 63 of the laser. Use of cell 61 results in a selective loss at the natural frequency referred to above and forces laser 12 to oscillate at a nearby frequency (2,948.8 cm$^{-1}$) which is attenuated only weakly by methane gas. Although the use of gas cell 61 provides an uncomplicated, relatively inexpensive manner for producing laser beam 13, lasers 10 and 12 may be replaced with a single helium-neon gas laser which is frequency tunable, for instance by known optical methods. Alternatively, a different type of laser, such as a tunable semiconductor diode laser may be employed.

Reference detectors 64 and 66 are utilized to monitor the power output from lasers 10 and 12, respectively, to detect any changes therein which may take place, for instance, due to dust settling on the laser mirrors or aging of the plasma tubes. This is important since the photoacoustic signals produced by microphones 34 and 35 are directly proportional to laser power. The power of laser beams 11 and 13, as measured by detectors 64 and 66, is continuously relayed to data processing unit 40 so that the output signals from microphones 34 and 35 can be constantly corrected for changes in laser power. In addition, reference detectors 64 and 66 provide a method for determining whether lasers 10 and 12 and system 8 as a whole are operating properly.

Acoustic cells 20 and 21 are designed to continually receive gases recovered from drilling mud. The gases are removed from the mud by a conventional apparatus, not shown, and then piped to a four-way connector 68 which branches into inlet line 69 leading to inlet port 69E of cell 21 and line 69B leading to inlet port 69D of cell 20. After flowing through cells 20 and 21, the sample gas is exhausted by a vacuum pump 70A through outlet port 71A and by a vacuum pump 70B through outlet port 71B. Although cells 20 and 21 may typically assume various configurations, in one preferred form they are cylindrical in shape with their longitudinal axis aligned with beams 11 and 13. The cells include a cylindrical body 72 and end walls 73 having centered, Brewster angle windows 74 which permit low loss entrance of infrared laser beams 11 and 13 with very little resistance to or disturbance of the beams. Cells 20 and 21 may be protected with acoustic insulation, internal baffles and shielding material (not shown) to minimize background noise generated by the flowing gas and other external acoustic disturbances. Although some background noise is produced by the flow of gas through the cells, the signal can be readily adjusted by data processing unit 40 by measuring the background noise generated at transducers 34 and 35 when both laser beams 11 and 13 are blocked.

Pressure transducers or microphones 34 and 35 may be mounted on cells 20 and 21, for instance, centrally along the length of the cylindrical body 72. Transducers 34 and 35 sense the acoustic disturbance generated in the sample gas due to the absorbed laser energy from laser beams 11 and 13, respectively. Transducers 34 and 35 produce an output electrical signal which is linearly proportional to the laser induced pressure pulse which in turn is linearly proportional to the level of infrared laser beam energy absorbed by the gas sample.

Pressure transucers are widely commercially available, including the Bruel and Kjaer Model 4161 or the Knowles series BL and BT miniature microphones. Photoacoustic cells constructed with these transducers are very sensitive. For example, a conservative photoacoustic cell sensitivity of $10^{-4}$ cm$^{-1}$ mW would imply a detection limit of 10 parts per million for a typical hydrocarbon gas with an absorption coefficient of 10 cm$^{-1}$ atm$^{-1}$ using a 1 milliwatt laser. This is well within the requisite concentration sensitivity range required in the logging of hydrocarbons emitting from horizons penetrated during natural gas, oil well and coal bore hole drilling.

The accuracy of measuring the extent to which methane absorbs the energies of beams 11 and 13 may be enhanced by lowering the pressure of the sample gases within cells 20 and 21 below atmospheric pressure. Applicant has determined that utilizing a cell pressure of approximately 400 torr significantly improves the accuracy of the methane gas concentration measurements while not significantly increasing the complexity or sophistication of the equipment needed to supply sample gases to cells 20 and 21.

Within the operating range of the present invention, the output signal produced by transducers 34 and 35 are proportional to the level of laser beam energy absorbed by the gas sample which in turn is proportional to the concentration of the particular hydrocarbon gas component excited by laser beams 11 or 13, respectively. However, this linearity typically exists only when the gas sample within cell 20 contains small concentrations of the particular hydrocarbon gas component being tested so that almost all of the energy of beams 11 and 13 pass through cells 20 and 21 without being absorbed and the gas sample is uniformly excited. The relationship between the intensity of the infrared radiation of a particular laser beam transmitted through a sample cell of a length L to the intensity of the infrared radiation entering the sample is defined by Beer's Law, wherein:

$$I/I_O = e^{-\alpha NL}$$

I equals the intensity of the infrared radiation transmitted through the sample gas $I_o$ equals the intensity of the infrared radiation entering the sample gas $\alpha$ equals the absorption coefficient of the gas sample (cm$^{-1}$ atm$^{-1}$ or cm$^{-1}$ torr$^{-1}$)

N equals the pressure of the sample gas (torr or atm)

From photoacoustic absorption measurements of n-butane ($\alpha = 12$ cm$^{-1}$ atm$^{-1}$) in a cell 9.2 cm long, Dewey, Kamm and Hackett (Appl. Phys. Lett. 22, 633 (1973)) have determined that the microphone response was linear up to a 2 percent butane concentration. Hence for practical purposes $\alpha NL$ can reach values near 2.2 and still maintain reasonable linearity. In maintaining $\alpha NL$ below about 2, $\alpha$ is constant for a particular gas at a particular infrared radiation frequency and thus cannot be varied. The value of L, the length of absorption chambers 20 and 21, may be changed by providing two chambers of different lengths. The use of two different length chambers may provide an adequate dynamic response range for the various concentrations of hydrocarbon gases which may exist in the sample gas. The linear dynamic range of a second shorter cell, not shown, could be extended somewhat further by operation at a reduced total sample pressure as a means of reducing N. This second sample cell would be aligned with the primary absorption cells 20 and 21 and remain evacuated until an absorption level is reached in cell 20 and/or 21 which exceeds the linear operating range. At this time the central data processing and control unit 40 will close a gas entry valve, not shown, to cell 20 and/or 21 and allow a vacuum pump, not shown, to evacuate cell 20 and/or 21. The shorter cell would then be opened to the sample gas stream and the exhaust valve, not shown, on this cell adjusted to a predetermined opening. When the hydrocarbon gas content reaches a lower value, this procedure is reversed and cell 20 and/or 21 is used again and the shorter cell(s) closed off.

As an alternative, an auxiliary air source 75 could be used to supply additional air to cells 20 and 21 to decrease the value of N. The operation of the auxiliary air source is illustrated and described for cell 20, however it applies equally to cell 21. Auxiliary air from source 75 is piped to cell 20 through line 76A and inlet 78A. The timing and volume of air supplied by auxiliary source 75 is controlled by data processing unit 40. When the level of the total hydrocarbon gas or the particular hydrocarbon gas component being sensed increases to a predetermined concentration, the data processing unit actuates auxiliary air source 75 to inject additional dilution air into cell 20 thereby lowering the value of N which in turn maintains detection system 8 within its linear operating range. By use of auxiliary air source 74, the linearity of detection system 8 may be maintained through a wide dynamic range encompassing at least four orders of magnitude of hydrocarbon gas concentrations.

Data processing unit 40 receives the amplified electrical voltage signals from amplifiers 36 and 38, converts them into digital signals, and then utilizes the digital signals to compute the concentration of $C_1$–$C_6^+$ gases within cell 20 and the concentration of $C_2$–$C_6^+$ gases in cell 21. To this end, system 8 is first calibrated by measuring the output signals from transducers 34 and 35 and amplifiers 36 and 38 for a series of known concentrations of hydrocarbon gas mixtures contained within cells 20 and 21. Thereafter, the determined relationship between sample gas concentration and output signal voltage can be used to conveniently determine the concentration of $C_1$–$C_6^+$ gas from the output voltage signal which is synchronized with beam 11 and the concentration of $C_2$–$C_6^+$ gas from the output voltage signal which is synchronized with beam 13. Once the concentrations have been calculated, the concentration of methane gas within the cells may be computed by subtracting these two concentration values from each other.

As mentioned above, another useful numerical value which may be calculated by data processing unit 40 is a ratio characteristic of "dry" and "wet" gas deposits as determined by dividing the computed $C_1$–$C_6^+$ hydrocarbon gas concentration by the computed $C_2$–$C_6^+$ gas concentration. This information is indicative of the ratio of lighter molecular weight hydrocarbon gases, such as methane and ethane, to the heavier molecular weight hydrocarbon gases, such as propane, butane, hexane, and pentane, comprising the sample gas within cells 20, 21 and 48. It is known that for a given "dry" or "wet" gas ratio, the sample gas within cell 20 is composed of approximate proportions of constituent hydrocarbon gases, (Hunt, *Petroleum Geochemistry and Geology*, San Francisco: W. H. Freeman & Co., 1979). Thus, the "wet" and "dry" gas ratio can be used to compute a correction factor which may be employed to adjust the concentrations of propane, n-butane and $C_5^+$ gases obtained through measurement of the photoacoustic signals produced by beams 45 and 47.

The gas concentrations and ratios calculated by data processing unit 40 may be presented on display 42, which may take one of many common forms, such as a strip chart, a printed tape or a digital visual display. The output of display 42 can be used to alert geologists or engineers to the presence of potential natural gas and/or oil horizons or coal deposits while drilling an exploratory or development prospect.

Carbon dioxide laser 44 is tunable by a diffraction grating 46 which serves as one of the mirrors of the laser cavity. In the present invention, grating 46 is pivotable between a first position wherein laser 44 produces a third beam 45 in the infrared range at a frequency of approximately 1052 cm$^{-1}$ which is absorbed by propane, and the small quantities of pentane, hexane and heptane present, and a second position wherein the laser produces a fourth beam 47, also in the infrared region at a frequency of approximately 973 cm$^{-1}$ which is strongly absorbed by n-butane gas, but only weakly by other types of hydrocarbon gases. At either frequency, laser 44 produces approximately one watt average output power, which may be in the form of a continuous wave or a series of pulses. In the first position, grating 46 is highly reflective for the 1052 cm$^{-1}$ transition of laser 44, and deflects all other frequencies out of the optical cavity axis so that the laser operates at a single frequency.

Laser beam 45 is absorbed more strongly by propane than by either pentane or heptane. There is essentially no absorption of beam 45 by methane, ethane, or butane. Beam 45 is absorbed by hexane to a nearly equal extent as by propane. The pentane, hexane, and heptane content of natural gas and crude oil in the majority of producing oil and/or natural gas horizons as well as coal beds are sufficiently smaller than propane that the effective contribution of these three hydrocarbon gases to the absorption of beam 45 is small. Hence beam 45 is a reasonably specific probe for measuring propane despite overlapping absorption by pentane, hexane, and heptane.

On the other hand, applicants have determined that laser beam 47 is highly selectively absorbed by n-butane gas and weakly absorbed by all other types of hydrocarbon gases so that a n-butane absorption measurement using beam 47 has an even higher specificity than the propane measurement using beam 45.

In the present invention, the frequencies of third beam 45 and fourth beam 47 are achieved by utilizing the most abundant isotopic form $^{12}C^{16}O_2$ as the working medium of laser 44. However, it is to be understood that other isotopic forms of carbon dioxide may be used to produce laser beams of other frequencies which correspond to additional natural vibration frequencies of propane or n-butane gases or even to the natural frequencies of different types of hydrocarbon gases, such as ethane, pentane, or hexane. The laser frequencies produced by these other isotopic forms of carbon dioxide may have a higher selectivity for a given gas than the frequencies available from the most abundant isotopic form $^{12}C^{16}O_2$. For instance, applicants have determined that use of the isotope $^{14}C^{16}O_2$ permits the generation of a laser beam having a frequency of about 850 cm$^{-1}$ which is highly absorbed by ethane gas, and not absorbed to any appreciable extent by methane, n-butane or i-butane and only weakly absorbed by propane.

Sample air is routed from four-way connector 68 through line 80 to inlet port 82 of cell 48. Sample gas continuously circulates through cell 48 and then exits through outlet port 84. In construction, cell 48 may be similar to cells 20 and 21, discussed above. As with cells 20 and 21, a pressure transducer 56 is mounted on cell 48 to sense the acoustic disturbance generated in the sample gas due to absorption of energy from laser beams 45 and 47 by propane and n-butane molecules, respectively. Preferably transducer 56 is similar in construction and sensitivity to transducers 34 and 35, as described above. Moreover, auxiliary air from source 75 can be supplied to cell 48 through line 85 to dilute the sample gas contained therein as required so that transducer 56 operates within the range at which the output electrical voltage signal produced thereby is proportional to the concentration of the particular type of hydrocarbon gas being monitored within the cell.

At the frequencies of laser beams 45 and 47, water vapor and $CO_2$ gas contained in the sample gas stream and entering photoacoustic cell 48 can cause attenuation of the laser beams. For example, assuming a transducer sensitivity of approximately $10^{-7}$ cm$^{-1}$ and a laser power of approximately 1 watt, in the absence of water vapor and other interferences, transducer 56 is capable of detecting the presence of propane and n-butane in as small concentrations as 0.9 parts per million and 0.3 parts per million, respectively. However, if cell 48 contains water vapor, for instance at a partial pressure of 20 torr, the photoacoustic signal produced by the water vapor will equal the propane signal at 18 parts per million of propane while a concentration of 11 parts per million of n-butane will equal the signal contribution from water. This level of sensitivity is more than sufficient in most mud logging situations. However, a dessicator 86 may be interposed within sample gas inlet line 80 to remove water vapor contained therein. Applicant has determined that by lowering the water vapor content of the sample gas by a factor of 10 through use of dessicator 86, the system is capable of detecting propane and n-butane concentrations as small as 2 parts per million and 1 part per million, respectively.

Rather than using a dessicator to remove the water from the sample gas, other techniques may be employed, such as freezing the water vapor in a cryogenic trap (not shown). However, during freezing of the water, some of the heavier molecular weight hydrocarbons may also be removed.

Absorption of laser beams 45 and 47 by $CO_2$ gas contained in the sample can cause interference also. P. Perlmutter, S. Shtrikman and M. Slatkine in an article appearing in *Applied Optics,* Vol. 18, at 2267 (1979) have determined that at the laser frequencies of beams 45 and 47, the $CO_2$ gas has an absorption coefficient of about $3\times10^{-6}$ cm$^{-1}$ torr$^{-1}$. This value for the $CO_2$ absorption coefficient is considerably smaller than that for propane, n-butane, pentane, hexane and heptane at the frequencies of the two $CO_2$ laser beams 45 and 47. However, the applicants have determined that the $CO_2$ gas content of natural gas accumulations can reach several percent. Therefore, absorption signals due to $CO_2$ gas in the sample could equal or exceed those for pentane, for example, by virtue of the larger fractional content of $CO_2$ in the sample gas compared to pentane. This interference, however, still represents less than about 5 percent of the total absorption signal generated by beams 45 and 47. The $C_5^+$ aggregate signal is about four to five times larger than the $CO_2$ gas interference signal even from several percent $CO_2$ in the sample, which represents a conservatively large $CO_2$ fraction. Hence, the $C_5^+$ concentration in the presence of $CO_2$ gas can be estimated by combining the absorption data derived from measurements using beams 11 and 13 with the $CO_2$ laser signals from beams 45 and 47, as discussed earlier. A calibration factor indicative of the "wet" or "dry" nature of the gas sample is used to extract the aggregate $C_5^+$ concentration from the total absorption signal measured with beams 45 and 47. This total absorption signal contains a comparatively small contribution from $CO_2$ gas. If the $CO_2$ content of the gas sample is of concern, a separate $CO_2$ detector, such as a non-dispersive infrared type monitor, can be added to separately measure $CO_2$ concentrations.

As with transducers 34 and 35, the electrical output signal from transducer 56 is amplified by amplifier 60 and then transmitted to data processing unit 40. If laser 44 is of a continuous wave type, then a chopper 58 is utilized to transform the continuous beams produced by the laser into pulses which are efficiently amplified by amplifier 60. Chopper 58 is constructed somewhat similarly to chopper 28 in that it includes a rotating disc; however the disc only requires a single set of apertures to allow passage of laser beams 45 and 47 since the two beams travel along the same path. Data processing unit 40 senses the rotational speed of chopper 58 to synchronize itself with the chopper for proper timing of the detection of the electrical output signal outputted by transducer 56. If laser 44 is of a pulsed type, so that beams 45 and 47 are initially emitted in short pulses, chopper 58 is not needed and data processor 40 may be synchronized with laser 44 directly to provide the proper timing for signal processing.

Data processing unit 40 converts the amplified signals received from amplifier 60 into values corresponding to the concentration of propane and n-butane gas contained within photoacoustic cell 48. Processing unit 40 adjusts these computed values according to the "dry" or "wet" gas composition in the sample as determined from input signals received from absorption of laser beams 11 and 13, as discussed above. Data processing unit 40 then transmits these adjusted values to display 42 for visual output for the use of the geologist or petroleum engineer. As with photoacoustic cells 20 and 21, when the concentration of the monitored gas exceeds the linear operating range of cell 48, processing unit 40 activates or deactivates auxiliary air source 75 to initiate or terminate a flow of additional air to photoacoustic cell 48 to maintain the concentration of the sample gas at the proper level for linear operation transducer 56, as previously discussed.

A certain fraction of the absorption of beams 45 and 47 is due to the $C_5^+$ gases. Thus, the concentration of $C_5^+$ gases can be calculated by data processing unit 40 from the same signals received from amplifier 60 used to calculate the propane and n-butane concentrations.

Moreover, the computed $C_5+$ gas concentration can also be adjusted according to the extent of dry or wet gas composition in the sample through the use of laser beams 11 and 13, as described above, relative to adjusting the initially computed propane and n-butane gas concentrations.

A fourth photoacoustic cell 88 having a transducer 57 mounted thereon can be used in conjunction with laser 44 to serve as a reference cell to calibrate the response signals produced by transducer 56. As shown, cell 88 is disposed in front of cell 48 and filled with a relatively low concentration of a known hydrocarbon gas mixture so that very little attenuation of the laser beams 45 and 47 occurs. The ratios of the output signals produced by transducers 57 and 56 obtained from the reference and sample cells, respectively, for an identical hydrocarbon gas mixture in each cell, calibrates the absolute response of transducer 56 and thereby cell 48.

A reference detector 90 is disposed in front of cell 88 to monitor the power output from laser 44 and transmit this information to data processing unit 40. Detector 90 serves as a primary standard to determine the power emitted by laser 44. The output signal produced by transducer 56 is directly proportional to the power output of laser 44 and the hydrocarbon gas content of the sample gas stream. Thus, as the power output of the laser varies, the signal received by processing unit 40 from amplifier 60 must be continually corrected so that accurate measurements of the gas concentrations within cell 48 may be made. Moreover, detector 90 serves to verify that not only laser 44, but also detector system 8 as a whole, is operating properly. Cell 88 and detector 90 are somewhat redundant means for tracking the output power of laser 44 and in practice only one of these would usually be used.

It is to be understood that the propane and n-butane content within cell 48 may be measured by laser 44 itself without the use of lasers 10 and 12. Although use of laser 44 by itself will eliminate the "dry" and "wet" gas correction factor, in some applications this may not be critical.

In the operation of hydrocarbon detection system 8, the responses of transducers 34 and 35 are calibrated by placing a series of hydrocarbon gas mixture samples of known composition within cells 20 and 21 and measuring the output signals produced by the transducers. The response of transducer 56 is calibrated by placing known concentrations of propane and n-butane gas within cell 48 and measuring the output signals produced by transducer 56 at each of the different gas concentrations. These measured calibration factors are dependent on the laser output powers from lasers 10, 12 and 44. The means for tracking the output powers from these lasers is provided by reference detectors 64, 66 and 90 and cell 88.

The above-described method and apparatus for mud logging of wells drilled for oil or natural gas not only detects the presence of most hydrocarbon gases and vapors, but also identifies the most significant hydrocarbon gas components, i.e. methane, propane, and n-butane, which are associated with oil and natural gas horizons, thus leading to vastly improved prediction and detection of the presence of oil and natural gas. The same instrumentation and method is used to measure the presence of methane which when correlated with the coal particles recovered from drill cuttings will delineate coal seams encountered during coal bore hole drilling. Moreover, by use of the present invention, the composition of the gases recovered from a mud stream from wells drilled for oil and natural gas as well as coal bore holes are analyzed in real time so that the depth at which oil and natural gas horizons or coal deposits are located can be accurately established as the drill penetrates these formation horizons. Also, the present invention has a wide dynamic operating range permitting the hydrocarbon gas components contained in the sample gas to be measured quantitatively even though the component concentrations may vary by several orders of magnitude. Thus, such quantitative analysis may differentiate among oil bearing, wet gas and dry gas horizons, as well as non-commercial pockets of methane gas.

As will be apparent to those skilled in the art to which the invention is addressed, the present invention may be embodied in forms and in methods other than those specifically disclosed above without departing from the spirit or essential characteristics of the invention. The particular steps of the hydrocarbon gas component detection method and the particular embodiments of the detection system 8, as described above, are therefore to be considered in all respects as illustrative and not restrictive, with the scope of the present invention being set forth in the appended claims rather than being limited to the foregoing description.

What is claimed is:

1. A method of determining the composition of hydrocarbon gases extracted during drilling operations, comprising the steps of:
   (a) directing a first laser beam at a frequency strongly absorbed by methane gas and other hydrocarbon gases at a sample of the extracted gas;
   (b) measuring the absorption of the first laser beam by the sample of gas;
   (c) directing a second laser beam at the sample of gas at a frequency weakly absorbed by methane gas;
   (d) measuring the absorption of the second laser beam by the sample of gas;
   (e) calculating the concentration of methane gas present in the gas sample based on the absorption of the first and second laser beams by the sample of gas;
   (f) directing a third laser beam at a sample of such gas at a frequency strongly absorbed by an additional type of hydrocarbon gas;
   (g) measuring the absorption of the third laser beam; and
   (h) calculating the concentration of the additional type of hydrocarbon gas present in the sample of gas based on the level of absorption of the third laser beam.

2. The method according to claim 1, wherein the step of directing the first laser beam includes directing the first laser beam at a flowing stream of the extracted gas sample.

3. The method of claim 1, wherein the step of measuring the absorption of the first laser beam by the gas sample includes:
   placing the gas sample in a photoacoustic absorption cell; and
   sensing the energy of the acoustic disturbance induced in the gas sample while being subjected to the first laser beam.

4. The method of claim 3, further including the step of producing a first output signal representative of the energy of the acoustic disturbance induced in the gas sample by the first laser beam.

5. The method of claim 3, wherein the sample of gas contained within the photoacoustic cell is at less than atmospheric pressure.

6. The method of claim 3, wherein a stream of the gas sample is circulated through the photoacoustic cell.

7. The method of claim 1, wherein the step of directing the second laser beam includes directing the second laser beam at a flowing stream of the extracted gas sample.

8. The method of claim 1, wherein the step of measuring the absorption of the second laser beam by the gas sample includes:
   placing the gas sample in a photoacoustic absorption cell; and
   sensing the energy of the acoustic disturbance induced in the gas sample while being subjected to the second laser beam.

9. The method of claim 8, further including the step of producing a second output signal representative of the energy of the acoustic disturbance induced in the gas sample by the second laser beam.

10. The method of claim 8, wherein the sample of gas contained within the photoacoustic cell is at less than atmospheric pressure.

11. The method of claim 8, wherein the step of placing the gas sample in the photoacoustic absorption cell includes circulating a stream of the gas sample through the photoacoustic cell.

12. The method of claim 1, wherein the step of directing the third laser beam includes directing the third laser beam at a flowing stream of the extracted gas sample.

13. The method of claim 1, wherein the step of measuring the absorption of the third laser beam by the sample of gas includes:
   placing the gas sample in a photoacoustic absorption cell; and
   sensing the energy of the acoustic disturbance induced in the gas sample while being subjected to the third laser beam.

14. The method of claim 13, further including the step of producing a third output signal representative of the energy of the acoustic disturbance induced in the gas sample by the third laser beam.

15. The method of claim 13, wherein the sample of gas placed within the photoacoustic absorption cell is at less than atmospheric pressure.

16. The method of claim 13, wherein the step of placing the gas sample in the photoacoustic absorption cell includes circulating a stream of the gas sample through the photoacoustic cell.

17. The method of claim 1, further including adjusting the calculated concentration of the additional type of hydrocarbon gas based on the level at which the first and second laser beams are absorbed by the sample of gas.

18. The method of claim 17, wherein the step of adjusting the calculated concentration of the additional type of hydrocarbon gas includes:
   calculating the wet or dry gas composition range by dividing the level of absorption of the first laser beam by the level of absorption of the second laser beam;
   based on the calculated wet or dry gas composition range, computing a compensation factor representative of the proportion of heavier hydrocarbon gases present in the sample of gas; and
   using the compensation factor to adjust the initially determined concentration of the additional type of hydrocarbon gas.

19. The method of claim 1, further including calculating the aggregate concentration of hydrocarbon gases having molecular weights heavier than the additional type of hydrocarbon gas present in the sample of gas.

20. The method of claim 19, further including using the measured absorption of the first, second and third laser beams to calculate the aggregate concentration of hydrocarbon gases having molecular weights heavier than the additional type of hydrocarbon gas present in the sample of gas.

21. The method of claim 20, wherein the step of calculating the aggregate concentration of hydrocarbon gases present in the sample of gas which are heavier than the additional type of hydrocarbon gases includes:
   using the measured absorption of the third laser beam to make an initial estimation of the concentration of the additional type of hydrocarbon gas concentration present in the sample of gas;
   using the estimation of the additional type of hydrocarbon gas concentration to make an initial estimation of the aggregate hydrocarbon gas having molecular weights heavier than the additional type of hydrocarbon gas present in the sample of gas;
   calculating the wet or dry composition range by dividing the level of absorption of the first laser beam by the level of absorption of the second laser beam;
   based on the calculated wet or dry gas composition range, computing a compensation factor representative of the aggregate concentration of hydrocarbon gases having molecular weights heavier than the additional type of hydrocarbon gas present in the sample of gas; and
   using the compensation factor to adjust the initially determined concentration of aggregate hydrocarbon gases present in the gas sample which have molecular weights heavier than the molecular weight of the additional type of hydrocarbon gas.

22. The method of claim 1, further including calculating the total amount of hydrocarbon gas present in the sample of gas based on the absorption of the first and second laser beams.

23. The method of claim 1, further including calculating the amount of total hydrocarbon gas less the amount of methane gas present in the sample of gas based on the absorption of the first and second laser beams.

24. The method of claim 1, wherein the step of directing the third laser beam includes directing the third laser beam at the sample of gas at a frequency strongly absorbed by propane gas.

25. The method of claim 24, wherein the step of measuring the level of absorption of the third laser beam includes:
   passing a flowing stream of the gas sample through a photoacoustic absorption cell;
   sensing the energy of the acoustic disturbance induced in the gas sample stream while being subjected to the third laser beam; and
   producing an output signal representative of the level of acoustic disturbance induced in the gas sample stream by the third laser beam.

26. The method of claim 24, further including adjusting the calculated concentration of the propane gas by using the levels of the first and second laser beams absorbed by the sample of gas.

27. The method of claim 26, wherein the step of adjusting the concentration of propane gas includes:
calculating the wet or dry gas composition range by dividing the level of absorption of the first laser beam by the level of absorption of the second laser beam;
based on the calculated wet or dry gas composition range, computing a compensation factor representative of the proportion of heavier hydrocarbon gases present in the sample of gas; and
using the compensation factor to adjust the initially determined propane gas concentration.

28. The method of claim 24, further including using the measured absorption of the first, second and third laser beams to calculate the aggregate concentration of pentane and heavier molecular weight hydrocarbon gases present in the gas sample.

29. The method of claim 28, wherein the step of calculating the concentration of pentane and heavier molecular weight hydrocarbon gases present in the gas sample includes:
using the measured level of absorption of the third laser beam to make an initial estimation of the propane gas concentration;
using the estimation of the propane gas concentration to make an initial estimation of the aggregate pentane and heavier molecular weight hydrocarbon gas concentrations;
calculating the wet or dry compensation range by dividing the level of absorption of the first laser beam by the level of absorption of the second laser beam;
based on the calculated wet or dry gas compensation range, computing a compensation factor representative of the heavier hydrocarbon gases present in the sample of gas; and
using the compensation factor to adjust the initially determined pentane and heavier molecular weight hydrocarbon gas concentration.

30. The method of claim 1, wherein the step of directing the third laser beam includes directing the third laser beam at the gas sample at a frequency strongly absorbed by n-butane gas.

31. The method of claim 30, wherein the step of measuring the level of absorption of the third laser beam by the sample of gas includes:
passing a flowing stream of the gas sample through a photoacoustic absorption cell;
sensing the energy of the acoustic disturbance induced in the gas sample while being subjected to the third laser beam; and
producing an output signal representative of the energy of the acoustic disturbance induced in the gas sample by the third laser beam.

32. The method of claim 30, further including using the measured absorptions of the first and second laser beams by the gas sample to adjust the calculated concentrations of n-butane gas.

33. The method of claim 32, wherein the step of adjusting the calculated concentration of n-butane gas includes:
calculating the wet or dry gas composition range by dividing the total hydrocarbon gas absorption measured with the first laser beam by the absorption measured using the second laser beam;
based on the calculated wet or dry gas composition range, computing a compensated factor representative of the proportion of heavier hydrocarbon gases present in the gas sample; and
using the compensation factor to adjust the initially calculated n-butane gas concentration.

34. A method of determining the composition of hydrocarbon gases in a sample of gas, comprising the steps of:
(a) directing a first laser beam at a frequency strongly absorbed by methane gas and other hydrocarbon gases at the sample of gas;
(b) measuring the absorption of the first laser beam by the sample of gas;
(c) directing a second laser beam at the sample of gas at a frequency weakly absorbed by methane gas;
(d) measuring the absorption of the second laser beam by the sample of gas;
(e) calculating the concentration of methane gas present in the gas sample based on the absorption of the first and second laser beams by the sample of gas;
(f) directing a third laser beam at a sample of such gas at a frequency strongly absorbed by propane gas;
(g) measuring the absorption of the third laser beam by the sample of gas;
(h) calculating the concentration of propane gas present in the sample of gas based on the level of absorption of the third laser beam;
(i) directing a fourth laser beam at the sample of gas at a frequency strongly absorbed by n-butane gas;
(j) measuring the absorption of the fourth laser beam by the sample of gas; and
(k) calculating the concentration of n-butane gas present in the sample of gas based on the absorption of the fourth laser beam.

35. The method of claim 34, wherein the step of measuring the level of absorption of the first laser beam energy by the gas sample includes:
placing the sample of gas in a photoacoustic absorption cell; and
sensing the energy of the acoustic disturbance induced in the gas sample while being subjected to the first laser beam.

36. The method of claim 35, further including producing a first output signal related to the energy of the acoustic disturbance induced in the sample of gas by the first laser beam.

37. The method of claim 35, wherein the step of placing the sample of gas in the photoacoustic cell includes maintaining the sample of gas at less than atmospheric pressure.

38. The method of claim 35, wherein the step of placing the sample of gas in the photoacoustic cell includes circulating a stream of the sample of gas through the cell.

39. The method of claim 34, wherein the step of measuring the level of absorption of the second laser beam energy by the sample of gas includes:
placing the sample of gas in a photoacoustic absorption cell; and
sensing the energy of the acoustic disturbance induced in the sample of gas while being subjected to the second laser beam.

40. The method of claim 39, further including producing a second output signal related to the energy of the acoustic disturbance induced in the sample of gas by the second laser beam.

41. The method of claim 39, wherein the step of placing the sample of gas in the photoacoustic cell includes maintaining the sample of gas at less than atmospheric pressure.

42. The method of claim 39, wherein the step of placing the sample of gas in the photoacoustic cell includes circulating a stream of the sample of gas through the cell.

43. The method of claim 34, wherein the step of measuring the level of the third laser beam energy absorbed by the sample of gas includes:
   placing the sample of gas in a photoacoustic absorption cell; and
   sensing the energy of the acoustic disturbance induced in the sample of gas while being subjected to the third laser beam.

44. The method of claim 43, further including producing a third output signal representative of the energy of the acoustic disturbance induced in the sample of gas by the third laser beam.

45. The method of claim 43, wherein the step of placing the sample of gas in the photoacoustic cell includes maintaining the sample of gas at less than atmospheric pressure.

46. The method of claim 43, wherein the step of placing the sample of gas in the photoacoustic cell includes circulating a stream of the sample of gas through the cell.

47. The method of claim 34, further including adjusting the calculated concentration of propane in the sample of gas based on the levels of absorption of the first and second laser beams.

48. The method of claim 47, wherein the step of adjusting the calculated concentration of propane gas present in the gas sample includes:
   using the measured level of the third laser beam absorbed by the sample of gas to make an initial estimation of the propane gas concentration;
   calculating the wet or dry gas composition range by dividing the level of absorption of the first laser beam by the level of absorption of the second laser beam;
   based on the calculated wet or dry gas composition range, computing a compensation factor representative of the proportion of heavier hydrocarbon gases present in the gas sample; and
   using the compensation factor to adjust the initially determined propane gas concentration.

49. The method of claim 34, wherein the step of measuring the level of the fourth laser beam energy absorbed by the sample of gas includes:
   placing the sample of gas in a photoacoustic absorption cell; and
   sensing the energy of the acoustic disturbance induced in the sample of gas while being subjected to the fourth laser beam.

50. The method of claim 49, further including producing a fourth output signal representative of the energy of the acoustic disturbance induced in the sample of gas by the fourth laser beam.

51. The method of claim 49, wherein the step of placing the sample of gas in the photoacoustic cell includes maintaining the sample of gas at less than atmospheric pressure.

52. The method of claim 49, wherein the step of placing the sample of gas in the photoacoustic cell includes circulating a stream of the sample of gas through the cell.

53. The method of claim 34, further including adjusting the calculated concentration of n-butane in the sample of gas based on the levels of absorption of the first and second laser beams.

54. The method of claim 53, wherein the step of adjusting the calculated concentration of n-butane gas present in the gas sample includes:
   using the measured absorption of the fourth laser beam absorbed by the gas sample to make an initial estimate of the n-butane gas concentration;
   calculating a wet or dry gas composition range by dividing the level of absorption of the first laser beam by the level of absorption of the second laser beam;
   based on the calculated wet or dry gas composition range, computing a compensation factor representative of the proportion of heavier hydrocarbon gases present in the gas sample; and
   using the compensation factor to adjust the initially determined n-butane gas concentration.

55. The method of claim 34, further including the step of presenting the concentration of methane gas, the concentration of propane gas and the concentration of n-butane gas present in the sample of gas on a visible display.

56. The method of claim 34, further including calculating the aggregate concentration of pentane and heavier molecular weight hydrocarbon gases present in the sample of gas.

57. The method of claim 56, further including using the measured absorption of the first, second and third laser beams to calculate the aggregate concentration of pentane and heavier molecular weight hydrocarbon gases.

58. The method of claim 57, wherein the step of calculating the concentration of pentane and heavier molecular weight hydrocarbon gases present in the gas sample includes:
   using the measured level of the third laser beam absorbed by the gas sample to make an initial estimation of the propane gas concentration;
   using the estimation of the propane gas concentration to make an initial estimation of the aggregate pentane and heavier molecular weight hydrocarbon gas concentration;
   calculating the wet or dry composition range by dividing the level of absorption of the first laser beam by the level of absorption of the second laser beam;
   based on the calculated wet or dry gas composition range, computing a compensation factor representative of the heavier hydrocarbon gases and vapors present in the gas sample; and
   using the compensation factor to adjust the initially determined pentane and heavier molecular weight hydrocarbon concentration.

59. A method for determining the constituent hydrocarbon gas composition of gases recovered from drilling mud removed from an oil or natural gas well or from effluent recovered from a coal bore hole, comprising the steps of:
   (a) passing a flowing stream of the gas sample recovered from the drilling mud or effluent through a first photoacoustic absorption cell;
   (b) directing a first laser beam at a frequency strongly absorbed by all common hydrocarbon gases and vapors at the first photoacoustic absorption cell;
   (c) sensing the energy of the acoustic disturbance generated within the first photoacoustic cell from absorption of the energy of the first laser beam by the gas sample stream;

(d) using the energy of the acoustic disturbance induced by the first laser beam to compute the total amount of hydrocarbon gases and vapors present in the sample;

(e) passing a flowing stream of the sample of gas through a second photoacoustic cell;

(f) directing a second laser beam at a second photoacoustic cell at a frequency weakly absorbed by methane and absorbed to about the same degree as the frequency of the first laser beam by the other hydrocarbon gases;

(g) sensing the energy of the acoustic disturbance generated within the second photoacoustic cell from absorption of the energy of the second laser beam by the gas sample stream;

(h) using the energy of the acoustic disturbance induced by the second laser beam to compute the amount of hydrocarbon gas less methane gas present in the gas sample;

(i) passing a flowing stream of the gas sample through a third photoacoustic cell;

(j) directing a third laser beam at the third photoacoustic cell at a frequency strongly absorbed by propane gas;

(k) sensing the energy of the acoustic disturbance generated within the third acoustic cell from absorption of the energy of the third laser beam by the gas sample;

(l) using the energy of the acoustic disturbance induced by the third laser beam to compute the amount of propane gas in the gas sample;

(m) directing a fourth laser beam at the third acoustic cell at a frequency strongly absorbed by n-butane gas;

(n) sensing the energy of the acoustic disturbance generated within the third photoacoustic cell from absorption of the energy of the fourth laser beam by the gas sample; and (o) using the energy of the acoustic disturbance induced by the fourth laser beam to compute the amount of n-butane gas contained in the gas sample.

60. The method of claim 59, further including the step of modulating the first and second laser beams to strike the first and second acoustic cells in short beam pulses, and modulating the third and fourth laser beams to alternatively strike the third acoustic cell in short beam pluses.

61. The method of claim 59, further including the step of adding auxiliary air to the first, second and third acoustic cells based on the level of the first, second, third and fourth output signals to maintain within a predetermined range the concentration of hydrocarbon gases within the first, second and third acoustic cells.

62. The method of claim 59, further including:
(a) diverting the gas sample stream from the first photoacoustic absorption cell to a fourth photoacoustic absorption cell of a length different from the length of the first cell;
(b) directing the first laser beam at the fourth cell;
(c) sensing the energy of the acoustic disturbance generated within the fourth cell from absorption of the energy of the first laser beam by the gas sample stream;
(d) producing a fifth output signal representative of the energy of acoustic disturbance generated within the fourth cell by the first laser beam; and (e) using the fifth output signal to compute the total amount of hydrocarbon gas and vapors present.

63. The method of claim 59, further including:
(a) diverting the gas sample stream from the second photoacoustic cell to a fifth photoacoustic absorption cell of a length different from the length of the second cell;
(b) directing the second laser beam at the fifth photoacoustic cell;
(c) sensing the energy of the acoustic disturbance generated within the fifth photoacoustic cell from absorption of the energy of the second laser beam by the gas sample stream;
(d) producing a sixth output signal representative of the energy of the acoustic disturbance generated in the fifth acoustic cell by the second laser beam; and
(e) using the sixth output signal to compute the amount of hydrocarbon gas less methane gas present in the gas sample stream.

64. The method of claim 59, further including:
(a) diverting the sample gas stream from the third photoacoustic absorption cell to a sixth photoacoustic absorption cell of a length different from the length of the third cell;
(b) directing the third laser beam at the sixth photoacoustic cell;
(c) sensing the energy of the acoustic disturbance generated within the sixth cell from absorption to the energy of the third laser beam by the gas sample stream;
(d) producing a seventh output signal representative of the energy of the acoustic disturbance generated in the sixth acoustic cell by the third laser beam;
(e) using the fifth, sixth and seventh output signals to compute the concentration of propane gas in the gas sample stream;
(f) directing the fourth laser beam at the sixth acoustic cell;
(g) sensing the energy of the acoustic disturbance generated within the sixth photoacoustic cell from the absorption of the energy of the fourth laser beam by the sample gas stream;
(h) producing an eighth output signal representative of the energy of the acoustic disturbance generated in the sixth photoacoustic cell by the fourth laser beam; and
(i) using the fifth, sixth and eighth output signals to compute the amount of n-butane gas contained in the gas sample stream.

65. The method of claim 59, further including using the energy of the acoustic disturbance induced by the first, second and third laser beams to compute the amount of propane gas in the gas sample.

66. The method of claim 59, further including using the energy of the acoustic disturbance induced by the first, second and fourth laser beams to compute the amount of n-butane gas contained in the gas sample.

67. An apparatus for detecting and measuring the composition of hydrocarbon gases and vapors recovered during drilling operations, comprising:
(a) first laser beam generating means for directing a first laser beam at a sample of gas recovered from the earth at a first wave frequency which is strongly absorbed by most common hydrocarbon gases and vapors;
(b) second laser beam generating means for directing a second laser beam at the sample of gas at a second wave frequency which is absorbed by most common hydrocarbon gases and vapors, but weakly absorbed by methane gas;

(c) third laser beam generating means for directing a third laser beam at the gas sample at a third wave frequency which is strongly absorbed by another type of hydrocarbon gas other than methane; and (d) sensing means responsive to the levels of energies absorbed by the gas sample at the first, second and third laser beams.

68. The apparatus according to claim 67, further including adjusting means for adjusting the third output signal based on the levels of the first and second output signals.

69. The apparatus according to claim 67, wherein said third laser beam generating means directs the third laser beam at a frequency which is strongly absorbed by propane gas.

70. The apparatus according to claim 69, wherein said third laser means includes a carbon dioxide gas laser.

71. The apparatus according to claim 67, wherein the third laser beam generating means directs the third laser beam at a frequency which is strongly absorbed by n-butane gas.

72. The apparatus according to claim 71, wherein said third laser means includes a carbon dioxide gas laser.

73. The apparatus according to claim 67, further including means for containing the gas sample during operation of the first, second and third laser beam generating means.

74. The apparatus according to claim 73, wherein said container means includes a first photoacoustic absorption absorption cell disposed in the path of the first laser beam and a second photoacoustic absorption cell disposed in the path of the second laser beam.

75. The apparatus according to claim 74, wherein said sensing means includes first means for detecting the energy of the acoustic disturbance generated within the gas sample contained within said first and second photoacoustic cells as the first and second laser beams strike the gas sample.

76. The apparatus according to claim 75, wherein said first acoustic wave detecting means includes a pressure transducer disposed in acoustic disturbance receiving communication with each of said first and second photoacoustic cells to produce electrical signals representative of the energy of the acoustic disturbances induced within the gas sample by the first and second laser beams.

77. The apparatus according to claim 74, further including first switching means for modulating the first and second laser beams to strike the gas sample contained within said first and second acoustic cells at different times.

78. The apparatus according to claim 73, wherein:
said container means includes a third photoacoustic cell disposed in the path of the third laser beam; and
said sensing means includes second means for detecting the energy of the acoustic disturbance generated within the gas sample contained within said third photoacoustic cell as the third laser beam strikes the gas sample.

79. The apparatus according to claim 78, wherein said second acoustic energy detecting means includes a pressure transducer disposed in acoustic disturbance receiving communication with said third photoacoustic cell to produce electrical signals representative of the energy of the acoustic disturbance generated within the gas sample by the third beam.

80. The apparatus according to claim 73, further including means for circulating the sample gas through said container means.

81. The apparatus according to claim 67:
further including fourth laser beam generating means for directing a fourth laser beam at the sample of gas at a fourth wave frequency which is strongly absorbed by a further type of hydrocarbon gas other than methane and other than the type of gas which strongly absorbs the third laser beam; and
said sensing means is also responsive to the level of energy absorbed by the gas sample as the fourth laser beam strikes the gas sample to produce a fourth output signal proportional to the energy absorbed by the gas sample from the fourth laser beam.

82. The apparatus according to claim 81, wherein said third laser beam generating means directs the third laser beam at a frequency which is strongly absorbed by propane gas; and
said fourth laser beam generating means directs the fourth laser beam at a frequency which is strongly absorbed by n-butane gas.

83. The apparatus according to claim 81, wherein said third and fourth laser means comprises:
a single carbon dioxide gas laser; and
tuning means for tuning said single carbon dioxide gas laser between the frequencies of the third and fourth laser beams.

84. The apparatus according to claim 83, further including switching means for alternatively and momentarily blocking the path of the third and fourth laser beams to transform the third and fourth laser beams into pulses which are sensed by said sensing means.

85. The apparatus according to claim 81, further including additional means for containing the gas sample during operation of the third and fourth laser beam generating means.

86. The apparatus according to claim 85, wherein said additional container means includes a third photoacoustic absorption cell disposed in the paths of said third and fourth laser beams, and said sensing means includes second means for detecting the energy of the acoustic disturbance generated within said third photoacoustic cell as said third and fourth laser beams strike said gas sample.

87. The apparatus according to claim 86, wherein said second detecting means includes a microphone disposed in acoustic disturbance receiving communication with said third photoacoustic cell to produce an electrical signal representative of the energy acoustic disturbance generated within said third photoacoustic cell as said third and fourth laser beams strike said gas sample.

88. The apparatus according to claim 85, further including means for circulating a continuous stream of the gas sample through said additional container means.

* * * * *